United States Patent [19]
Mori et al.

[11] Patent Number: 5,221,796
[45] Date of Patent: Jun. 22, 1993

[54] GLYCEROL DERIVATIVES

[75] Inventors: Hideto Mori; Naoyuki Nishikawa, both of Minami-Ashigara, Japan

[73] Assignee: Fuji Photo Film Co., Ltd., Kanagawa, Japan

[21] Appl. No.: 833,559

[22] Filed: Feb. 11, 1992

[30] Foreign Application Priority Data

| Feb. 12, 1991 | [JP] | Japan | 3-18873 |
| Feb. 12, 1991 | [JP] | Japan | 3-18874 |
| Feb. 12, 1991 | [JP] | Japan | 3-18875 |
| Apr. 16, 1991 | [JP] | Japan | 3-84036 |

[51] Int. Cl.$^5$ .............................................. C07F 9/02
[52] U.S. Cl. .................................... 554/79; 554/80; 554/78; 554/227
[58] Field of Search ................ 554/80, 79, 78, 227

[56] References Cited
PUBLICATIONS

Chemical Abstracts, vol. 114, #3, 1991, p. 383, 20692c.
Chemical Abstracts, vol. 92, #7, 1980, p. 621, 58190c.
Chemical Abstracts, vol. 88, #13, 1978, p. 141, 84784m.
Chemical Abstracts, vol. 87, #23, 1977, p. 202, 179453w.
Chemical Abstracts, vol. 110, #15, 1989, p. 757, 135643y.

*Primary Examiner*—Jose G. Dees
*Assistant Examiner*—Deborah D. Carr
*Attorney, Agent, or Firm*—Sughrue, Mion, Zinn, Macpeak & Seas

[57] ABSTRACT

A glycerol derivative or a salt thereof is provided and the derivative is represented by the following general formula (I):

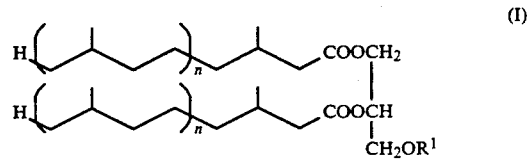

wherein n is an integer ranging from 1 to 3; $R^1$ represents a hydrogen atom or a group: $-P(O)(OR^2)(OR^3)$ wherein $R^2$ represents a hydrogen atom or a protective group for the phosphoric acid residue and $R^3$ represents a hydrogen atom, a protective group for the phosphoric acid residue or a hydrophilic group; provided that the phosphoric acid residue represented by $R^1$ may be in the form of a salt wih a proper counter ion; and, in respect of stereochemistry of asymmetric carbon atoms present in the molecule, the derivative or salt may be either an optically active isomer or a racemic isomer.

These compounds are excellent in biological compatibility, dispersibility and chemical stability and that they can provide membranes having high flowability and high barrier properties as compared with conventional phospholipids.

8 Claims, No Drawings

GLYCEROL DERIVATIVES

BACKGROUND OF THE INVENTION

The present invention relates to a novel glycerol derivative having special characteristics.

It has generally been known that when amphipathic molecules such as phospholipids are dispersed in water, they preferentially form molecular aggregates in a special shape. Among these, liposome is a closed endoplasmic reticulum formed from a bilayer of lipid and contains aqueous layer therein. For this reason, it has attracted special interest recently in the field of medicine and pharmacy and accordingly, many attempts have been directed to the use thereof as carriers for various medicines or as diagnostic agents through incorporation of water-soluble substances into the liposome (see, for instance, SUNAMOTO et al., Bioscience and Industry, 1989, 47, p. 475). In addition, attempts have also been directed to the use thereof in cosmetics while making use of the water retention and moisture retention characteristics of the liposome.

When phospholipids are dispersed in water to use them in the form of liposomes or emulsions, it is important that they can easily be dispersed in a certain medium to give a uniform dispersion and that the resulting dispersion surely has good stability. Therefore, it is a matter of course that materials having good dispersibility and stability should be selected and used in such applications. In case of liposome, for instance, the flowability of the liposome bilayer is greatly affected by temperature and it causes gel-liquid crystal phase transition. It has been known that the mobility of molecules present in a bilayer which is in a liquid crystalline state is substantially higher than that observed for molecules in a bilayer which is in a gel state with respect to all of lateral diffusion, flip-flop and exchange. In general, liposomes formed from lipids whose hydrophobic fatty acid residues have small numbers of carbon atoms and/or high degrees of unsaturation have high membrane flowability and on the contrary, those formed from lipids which are saturated and have relatively large numbers of carbon atoms have low flowability and rather high phase transition temperatures. Thus, it would be possible to control the membrane flowability of the liposome and the dispersibility of lipids as well as barrier properties of the membrane closely related to the flowability by adjusting the chain length and the degree of unsaturation of the fatty acid residues of lipids used.

For instance, lipids which comprise, as components, unsaturated fatty acids such as yolk phosphatidylcholine are in liquid crystal states at a temperature of not less than ordinary temperature because of low phase transition temperatures and accordingly form soft membranes. The lipids having unsaturated fatty acids are indispensable to living body since biological membranes in the liquid crystalline state serve as barriers. It can be assumed that the membranes of the organism would acquire the characteristics of this kind because it is advantageous that the membranes cause change in physical properties for relieving abrupt changes in various environmental conditions such as ambient temperature. This phenomenon is likewise important when the liposome is used as a carrier for medicines. For instance, when a hydrophobic medicine is incorporated into a liposome membrane, good dispersibility and high encapsulation efficiency can often be attained by the use of those comprising unsaturated fatty acids such as yolk phosphatidylcholine as compared with those simply comprising saturated fatty acids.

However, the polyvalent unsaturated fatty acids included in the yolk phosphatidylcholine are liable to undergo a peroxidation reaction with oxygen and thus are insufficient in the storage stability. For this reason, it is preferred to use phospholipids simply comprising saturated fatty acids which are hardly attacked by oxygen if the stability is regarded as of major importance. However, when a liposome is prepared using dimyristoyl phosphatidylcholine which is a naturally occurring saturated phospholipid as a membrane component, it is very difficult to hold glucose within the resulting liposome at the phase transition temperature thereof or higher. In addition, it has likewise been known that the liposome prepared from palmitoyl phosphatidylcholine alone is unstable and immediately causes aggregation and correspondingly precipitation. In general, the phospholipids comprising only saturated fatty acids are densely arranged, in particular at the phase transition temperature or lower and have low flexibility. As a result, they have a strong tendency such that they exclude foreign molecules and cause phase separation. Therefore, it is impracticable to prepare liposomes from the phospholipids simply comprising saturated fatty acids.

As has been discussed above, good dispersibility and good flowability of the liposomes are essentially contrary to the chemical stability thereof and it is impossible to simultaneously satisfy these three requirements. In other words, there have not yet been known any materials inclusive of the conventionally used phospholipids simply comprising saturated fatty acids and the phospholipids comprising unsaturated fatty acids which can satisfy these requirements at the same time.

Under such circumstances, the inventors of this invention have conducted various investigations for searching for substances which satisfy all of the foregoing requirements and as a result, the inventors have taken note of biomembranes of bacteria. In general, bacteria do not contain any polyvalent unsaturated fatty acid in the biomembranes unlike animals and plants. About 30 years ago, investigators in Japan discovered, for the first time, the presence of branched fatty acids (such as iso acid and anti-iso acid) as principal fatty acids for bacterial lipids (S. Akashi and K. Saito, J. Biochem., 1960, 47, p. 222). There have presently been known almost several hundred kinds of bacteria which possess such branched fatty acids as principal fatty acids in biological lipids (T. KANEDA, Bacteriol. Rev., 1977, 41, p. 391).

Recently, many diacyl phosphatidylcholines comprising various branched fatty acids have been synthesized using the structure of the foregoing branched fatty acid as a model and the phase transition temperatures thereof were determined. As a result, it is proved that the phase transition temperatures of lipids comprising branched fatty acids are about 16° to 28° C. lower than those of lipids comprising linear fatty acids. In other words, the branched fatty acids contribute to an increase in the flowability of bacterial biomembranes as compared with corresponding linear fatty acids (T. KANEDA, Bioscience and Industry, 1990, 48, p. 229). These branched fatty acids are considered to be desirable substances since they are hardly attacked by oxygen unlike the polyvalent unsaturated fatty acids and have high chemical stability. However, iso acid and anti-iso acid are not universarily present in the natural world and it is very difficult to purify and/or isolate them since they are present in the form of a mixture with other substances carrying hydrophobic moieties of various structures. Thus, the only means left is chemical synthesis thereof, but there is a limit in raw materials easily available. Moreover, the mass-production thereof is very difficult since a lot of processes are required for extending the carbon chain length.

To solve these problems, the biomembranes of archaebacteria have recently attracted special interest. The term "archaebacteria" is a recent concept proposed by Woese et al. in 1977 on the basis of the comparison between base sequences of 16s rRNA's of various organisms and there have presently been known three groups, i.e., highly halophilic bacteria, sulfur-dependent highly thermophilic bacteria and methane-producing bacteria (see Yosuke KOGA, "Archaebacteria", 1988, published by Tokyo University Publishing Society). All of the polar lipids of archaebacteria presently known are glycerolipids having ether bonds and most specific property thereof is that the hydrocarbon chains thereof are saturated isoprenoids having 20 or 40 carbon atoms. The saturated isoprenoids are likewise hardly attacked by oxygen and chemically stable. Thus, it can be anticipated that materials having special properties can be obtained if artificial lipids are designed and synthesized while using these lipids as models.

Chain isoprenoids are relatively easily available as compared with iso acid and anti-iso acid and accordingly, there have recently been reported various experimental results of lipids which have these isoprenoids introduced into the hydrophobic moieties thereof (K. Yamauchi et al., Biochem. Biophys. Acta, 1989, 1003, p. 151; K. Yamauchi et al., J. Am. Chem. Soc., 1990, 112, p. 3188; L. C. Stewart et al., Chem. Phys. Lipids, 1990,54, p. 115; YAMAUCHI et al., Collected Resume of Heisei 2 (1990) Spring Annual Meeting of Chemical Society of Japan, pp. 1793, 1794; TODA et al., Collected Resume of Heisei 2 (1990) Spring Annual Meeting of Chemical Society of Japan, p. 1793; R. A. Moss et al., Tetrahedron Lett., 1990, 31, p. 7559; and Japanese Unexamined Patent Publication (hereinafter referred to as "J. P. KOKAI") No. Hei 2-288849). It has consequently been found out that the lipid bilayers formed from isoprenoid type lipids have not only low phase transition temperatures but also high membrane barrier properties. However, in the molecular design of isoprenoid type artificial glycerolipids presently proposed, the glycerol moieties are linked to the hydrocarbon chain moieties through ether bonds similar to the biomembranes of archaebacteria. Therefore, the synthetic methods cannot widely be used because they are inconvenient for the mass-production thereof.

Further, there has been known an example in which a quaternary ammonium salt having an isoprenoid chain in lipid bilayers and lipid bilayers immobilized onto polymer films (see J. P. KOKAI No. Hei 2-288849). As a result, there have been found out that these lipid bilayers show flowability approximately identical to that of the biomembranes and that the film carrying the lipid bilayers immobilized thereon are soft and flexible and have excellent strength.

As has been discussed above in detail, all of the conventionally known phospholipids inclusive of those comprising only saturated fatty acids and those comprising unsaturated fatty acids do not satisfy all of the foregoing requirements simultaneously. It may be anticipated that lipids having branched fatty acids or chain isoprenoid skeletons, in particular, iso acid or anti-iso acid would exhibit promising characteristics, but it has been very difficult to isolate and purify them from the natural resorces and to chemically synthesize the same.

SUMMARY OF THE INVENTION

Accordingly, a first object of the present invention is to provide an isoprenoid type phospholipid exhibiting special characteristics which cannot be predicted from the conventionally used phospholipids comprising simply saturated fatty acids or those comprising unsaturated fatty acids.

A second object of the present invention is to provide a material which is an important intermediate capable of being widely used in the preparation of an isoprenoid type phospholipid having excellent biological compatibility, good dispersibility and high chemical stability, and further capable of providing a membrane having good flowability and high barrier properties, which cannot be predicted from phospholipids simply comprising saturated fatty acids or those comprising unsaturated fatty acids, and which can likewise form molecular aggregates by itself.

A third object of the present invention is to provide an isoprenoid type phospholipid which can be mass-produced, has excellent biological compatibility, good dispersibility and high chemical stability and is further capable of providing a membrane having good flowability and high barrier properties. These properties cannot be predicted from phospholipids simply comprising saturated fatty acids or those comprising unsaturated fatty acids.

The foregoing objects of the present invention can effectively be achieved by providing a glycerol derivative represented by the following general formula (I) or a salt thereof:

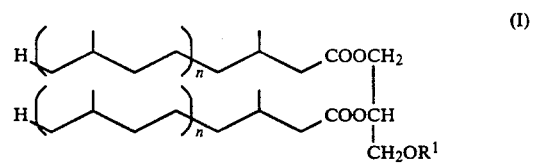

(I)

wherein n is an integer ranging from 1 to 3; $R^1$ represents a hydrogen atom or a group: $-P(O)(OR^2)(OR^3)$ (wherein $R^2$ represents a hydrogen atom or a protective group for the phosphoric acid residue; $R^3$ represents a hydrogen atom, a protective group for the phosphoric acid residue or a hydrophilic group, provided that the phosphoric acid residue represented by $R^1$ may form a salt with a proper counter ion); and in respect of stereochemistry of asymmetric carbon atoms present in the molecule, the derivative may be either optically active or racemic isomer.

DESCRIPTION OF THE PREFERRED EMBODIMENTS

As seen from the above, the isoprenoid type glycerol derivative of the present invention is characterized in that the hydrophobic moiety having the isoprenoid skeleton is linked to the glycerol moiety through an ester bond instead of an ether bond conventionally known.

The glycerol derivative has, as the carbon skeleton of the hydrophobic moiety, a monoterpene for n=1, a sesquiterpene for n=2 and a diterpene for n=3, but if the phospholipid of the present invention is used in the form of a lipid bilayer such as a liposome or an LB (lipid bilayer) film, n is preferably 3 while if the phospholipid is used in the form of micelle, n is preferably 1 or 2. Regarding the stereochemistry of asymmetric carbon atoms present in the molecule, the derivative may be either optically active or racemic isomer. They may arbitrarily be selected while taking availability of raw materials into consideration, but in respect of the stereochemistry of the branched methyl group on the hydrophobic part of the isoprenoid, those having absolute configuration (R) are preferably used as optically active isomers. Such optically active isomers can be prepared using naturally occurring terpenes as starting materials or by asymmetric hydrogen addition in accordance with the method of NOYORI et al. (J. Org. Chem., 1988, 53, p. 708 and J. Am. Chem. Soc., 1987, 109, p. 1596).

According to a first embodiment of the present invention, there is provided a compound represented by the following general formula (II):

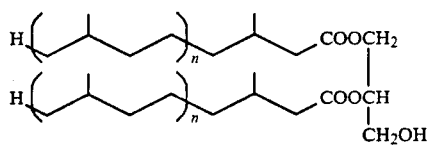

(II)

wherein n is an integer ranging from 1 to 3.

Specific examples of the compounds of Formula (II) are as follows, but the present invention is by no means limited to those specific ones:

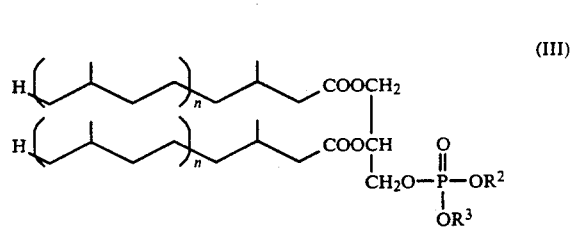

(III)

wherein n represents an integer ranging from 1 to 3.

$R^2$ and $R^3$ each independently represents a hydrogen atom or a protective group for the phosphoric acid residue. The protective groups may be selected from those usually known in the preparation of nucleic acids and phospholipids while taking, into consideration, various factors such as easiness of synthesis and conditions for deblocking. Specific examples thereof include benzyl, phenyl, o-chlorophenyl, p-chlorophenyl, methyl, 2,2,2-trichloroethyl, 2,2,2-tribromoethyl, 2-cyanoethyl, allyl and cyclopropylmethyl groups, with benzyl, phenyl and methyl groups being preferred.

Moreover, the phosphoric acid residue may be in the form of a salt with an appropriate counter ion, but it is preferred that the salt be physiologically and pharmaceutically acceptable. Specific examples of such salts are ammonium salt, alkali metal salts such as sodium and potassium salts, and alkaline earth metal salts such as magnesium and calcium salts. Among these, particularly preferred are sodium and potassium salts. The phosphoric acid residue can be converted into salts by any method currently used.

The compounds of Formula (III) of the present invention can be advantageously prepared by a method as disclosed in, for instance, H. Eibl, Chem. Phys. Lipids, 1980, 26, p. 405. Preparation methods can properly be selected in consideration of various factors such as easy availability of reagents used and scale of reaction.

Specific examples of the compounds of Formula (III) will be given below, but the present invention is not restricted to these specific examples.

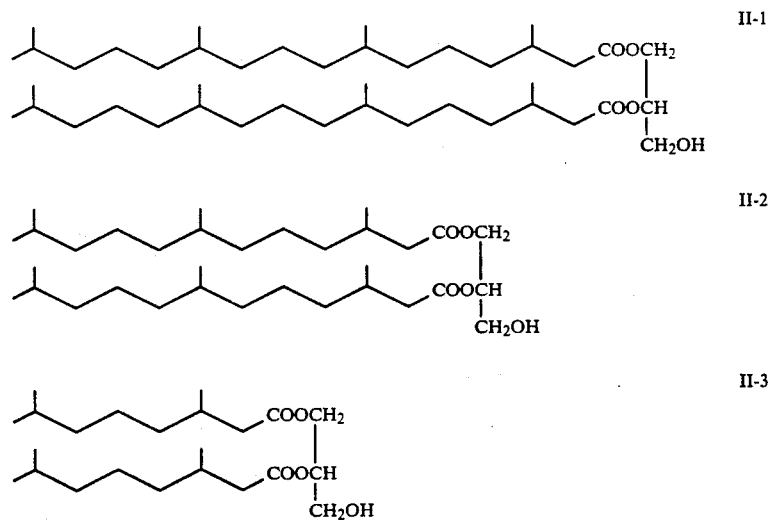

II-1

II-2

II-3

According to a second embodiment of the present invention, there is provided a compound represented by the following general formula (III):

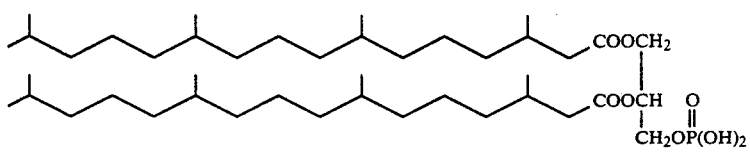

III-1

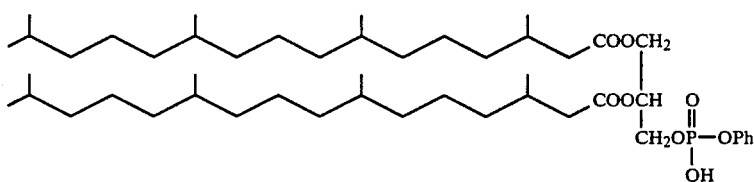

III-2

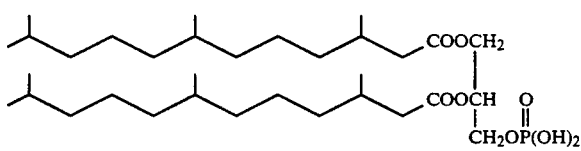

III-3

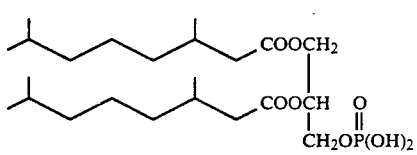

III-4

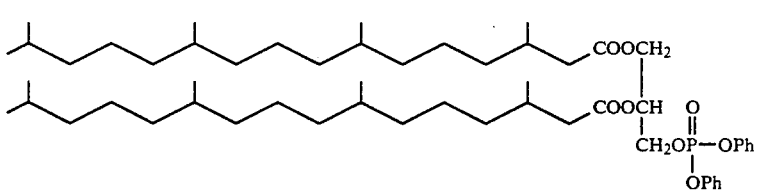

III-5

In the foregoing formulas, Ph represents a phenyl group.

According to a third embodiment of the present invention, there is provided a compound represented by the following general formula (IV):

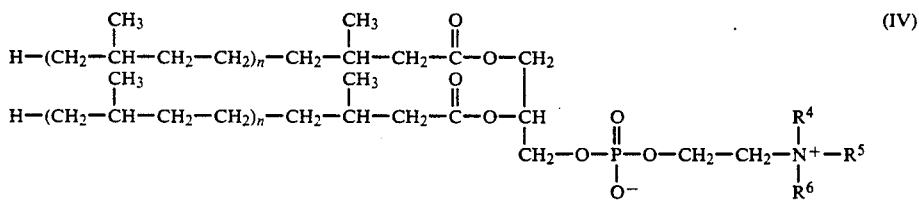

(IV)

wherein n is an integer of 1 to 3; $R^4$, $R^5$ and $R^6$ each represents a hydrogen atom or a lower alkyl group, provided that $R^4$, $R^5$ and $R^6$ do not represent hydrogen atoms at the same time. The term "lower alkyl group" mean an alkyl group having 1 to 5 carbon atoms such as a methyl or ethyl group. Further, regarding the stereochemistry of asymmetric carbon atoms present in the molecule, the compounds may be either optically active or racemic isomers.

The compounds of Formula (IV) of the invention can be prepared by any method for preparing a variety of phosphatidylcholine derivatives and simulants thereof. Examples thereof include semi-synthetic methods such as a method which comprises condensing glycerophosphocholine-cadmium chloride complex with a carboxylic acid having a chain corresponding to the desired hydrophobic chain in the presence of a condensation agent such as dicyclohexyl carbodiimide or acylating the complex with a carboxylic acid halide (such as chloride or bromide) having a chain corresponding to the desired hydrophobic chain of the resulting product (Can. J. Biochem. Physiol., 1959, 37, p. 953); a method comprising acylating with an acylimidazole (Chem. Phys. Lipids, 1981, 28, p. 111); a method comprising acylating with a fatty acid anhydride in the presence of 4-dimethylaminopyridine (J. Am. Chem. Soc., 1982, 104, p. 791); a method in which a fatty acid anhydride is used at a high temperature in the presence of a base (J. P. KOKAI No. Hei 1-172395); and a method comprising acylating glycerophosphocholine supported on a carrier with a fatty acid anhydride or a fatty acid halide (J. P. KOKAI Nos. Sho 61-207396, Sho 60-255798 and Hei 1-131190).

Besides, it is also possible to use other methods such as a method of Baer et al. (J.Am. Chem. Soc., 1950, 72, p. 942); a method of H. Eibl et al. in which corresponding dialkylglycerol and bromoethyl phosphodichloridate are employed (Liebigs Ann. Chem., 1967, 709, p.

226); and methods in which 2-chloro-2-oxa-1, 2,3-dioxaphosphorane is used (Bull. Soc. Chim. Fr., 1974, p. 667; ibid, 1975, p. 2326); as well as those in which the foregoing methods are applied, such as a method of R. L. Magolda (Tetrahedron Lett., 1985,26, p. 1167).

The carboxylic acids corresponding to hydrophobic chains can be prepared by hydrogenating natural or synthetic terpenes (such as geraniol, farnesol and phytol) as starting materials and then oxidizing the hydrogenated products; or subjecting these starting materials to asymmetric hydrogen addition and then oxidizing the products according to the method of NOYORI et al. (J. Org. Chem., 1988, 53, p. 708; and J. Am. Chem. Soc., 987, 109, p. 1596).

In the foregoing method, the hydrogenation can easily be carried out at room temperature in ethyl acetate or methanol in the presence of palladium-carbon or platinum dioxide as a catalyst. Particularly preferred is a method in which platinum dioxide is used as a catalyst. On the other hand, the oxidation can be performed by methods generally used such as a method in which ruthenium trichloride is used, Jones' oxidation (Organic Syntheses, Col. Vol. IV, p. 310, John Wiley & Sons Inc., New York, 1963) and a method using nitric acid, but particularly excellent results were obtained by the method in which ruthenium trichloride was used.

The use of diacylglycerol is required depending on the synthetic methods, but in this case, it is sufficient to acylating a carboxylic acid having a chain corresponding to the desired hydrophobic chain and an optically active or racemic benzylglycerol in the presence of a condensation agent such as dicyclohexylcarbodiimide or acylating with an acyl halide having a chain corresponding to the desired hydrophobic chain and then subjecting the resulting acylated product to hydrogenolysis.

According to a fourth embodiment of the present invention, there is provided a compound represented by the following general formula (V):

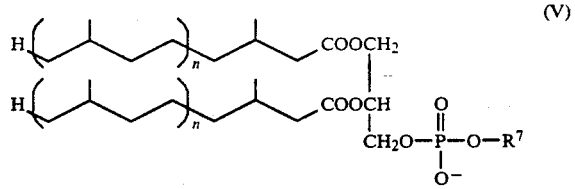

wherein n is an integer ranging from 1 to 3; $R^7$ represents a hydrophilic group. The term "hydrophilic group" herein used means that required for the compound of Formula (V) to form molecular aggregates such as liposomes or micelles. In general, the shape of the resulting molecular aggregate is determined by the balance between the hydrophilic group and the hydrophobic group in a lipid molecule and the overall shape of the molecule and there has been known the HLB (hydrophilic-lipophilic balance) value as an index for indicating the balance between the hydrophilicity and the hydrophobicity or lipophilicity of this amphipathic molecule. The higher the HLB value, the higher the hydrophilicity. Thus, substances having well-balanced hydrophilicity and hydrophobicity can form stable molecular aggregates such as liposomes.

The HLB value can likewise be obtained by the following equation:

$$HLB = 11.7 \log (Mw/Mo) + 7$$

Mo = molecular weight of the alkyl moiety;
Mw = (molecular weight of the substance) − Mo.

The amphipathic balance of the compound of the present invention can be defined by the HLB value. The compounds of the invention preferably has HLB values ranging from 2 to 18. The HL value is detailed in "KAGAKU NO RYOIKI (Regions of Chemistry)", 1953, 7, p. 689.

The hydrophilic groups which satisfy the foregoing requirements are, for instance, ethanolamine residue ($-CH_2CH_2NH_2$), serine residue ($-CH_2CH(NH_2)-COOH$), glycerol residue ($-CH_2CH(OH)-CH_2OH$) and myo-inositol residue represented by the following formula (VI):

The compounds of Formula (V) according to the present invention may be in the form of salts with appropriate counter ions (inclusive of intramolecular salts). It is preferred that these salts be physiologically and pharmaceutically acceptable. Specific examples thereof include salts with inorganic acids such as hydrochlorides, sulfates and nitrates; salts with organic acids such as acetates, trifluoroacetates, lactates and tartrates; and ammonium salts, sodium salts, potassium salts, magnesium salts and calcium salts. Among these, particularly preferred are hydrochlorides, acetates, trifluoroacetates and sodium salts. These salts can be obtained in the usual manner.

Specific examples of the compounds of Formula (V) will be given below, but the present invention is by no means limited to these specific ones.

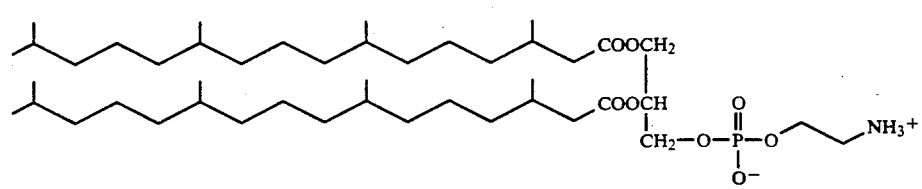

V-1

V-2
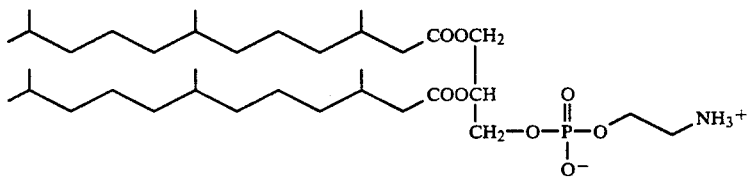

V-3
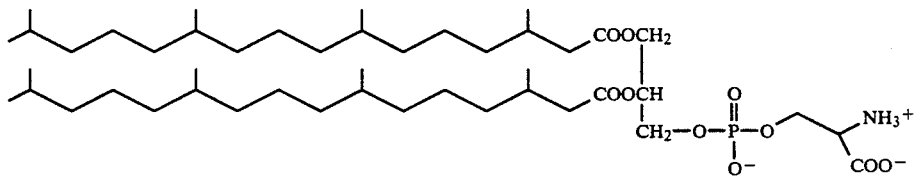

V-4
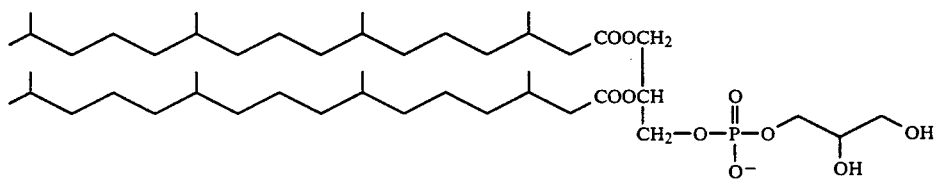

V-5
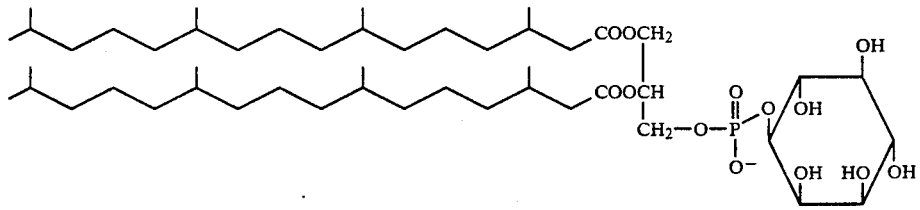

Then the synthesis of Compounds (V) of the present invention will be explained below while taking the exemplified compound V-1, i.e., phosphatidylethanolamine by way of example. Compound V-1 can be prepared by synthesizing diacylglycerol represented by the foregoing formula II-1 corresponding to the hydrophobic moiety and a protected ethanolamine represented by the formula: $HOCH_2CH_2NHR^8$ corresponding to the hydrophilic moiety, reacting, in order, the resulting products with a bifunctional agent for forming a phosphoric acid ester represented by the formula: $R^9OPOCl_2$ and then removing the protective groups.

$R^8$ represents a protective group for the amino group. Such protective groups for amino group may be any known ones, but they should be selected while taking, into consideration, various factors such as properties of intended products and conditions for deblocking. Preferred protective groups for amino group are, for instance, t-butoxycarbonyl and benzyloxycarbonyl groups.

$R^9$ represents a protective group for phosphoric acid. Specific examples thereof are the same as those defined above in connection with the substituents $R^2$ and $R^3$.

According to an alternative method, the compounds of Formula (V) of the present invention can likewise be prepared by, for instance, converting diacylglycerol represented by Formula II-1 into a phosphatidic acid derivative of Formula III-1, condensing the derivative with a separately prepared hydrophilic moiety using a condensation agent and then removing the protective group. The condensation is preferably carried out using arenesulfonyl chlorides as condensation agents. Condensation agents most commonly used are, for instance, those carrying bulky substituents such as trimethylbenzenesulfonyl chloride and triisopropylbenzenesulfonyl chloride.

The following reaction scheme 1 shows an illustrative route of synthesis of Compound II-1 and Compound V-1 which is prepared through Compound II-1 as an intermediate. In addition, the following reaction scheme 2 shows an illustrative route of synthesis of Compound III-5 and Compound III-1 which are obtained through Compound II-1 as an intermediate as well as an illustrative route of synthesis of Compound V-1 through Compound III-1 (phosphatidic acid) as an intermediate. In these reaction schemes, various solvents, protective groups and reagents are expressed in terms of abbreviations currently used.

Scheme 1

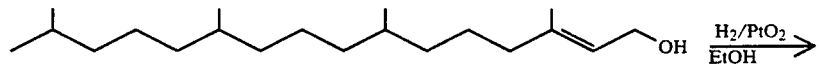

-continued
Scheme 1
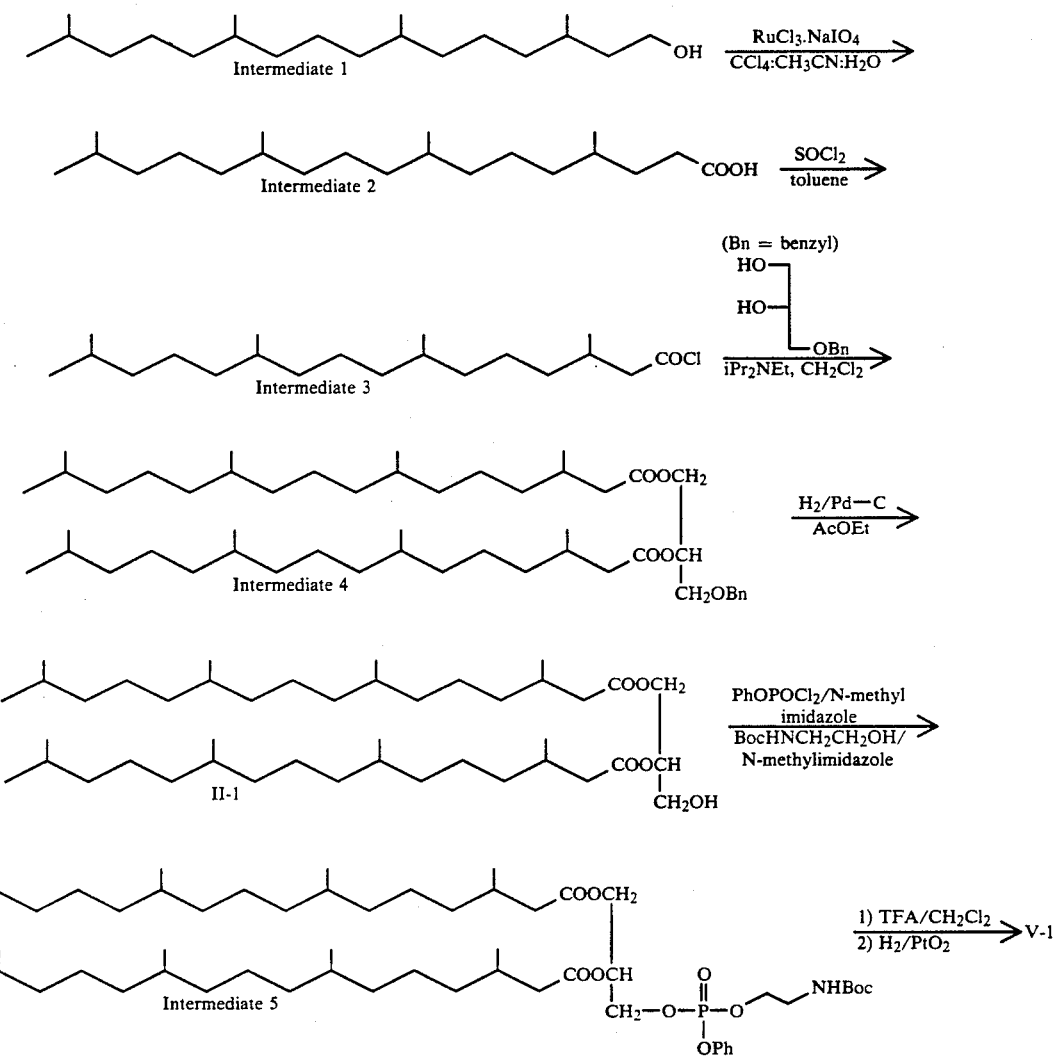
Scheme 2
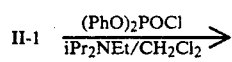
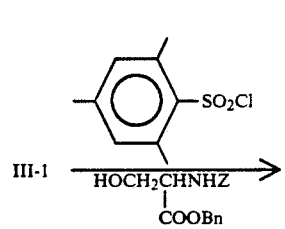

-continued
Scheme 2

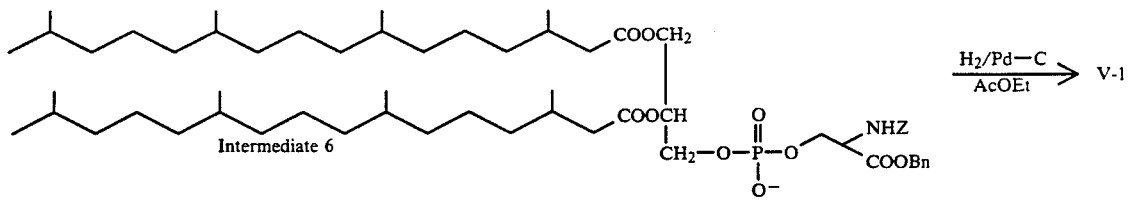

The methods for synthesizing the compounds of Formula (V) of the present invention have been explained while taking specific compounds by way of examples, but these compounds can of course be prepared by other methods. Such other methods are all detailed in, for instance, H. Eibl, Chem. Phys. Lipids, 1980, 26, p. 405 and can likewise be employed in the preparation of phosphatidylserine, phosphatidylglycerol and phosphatidylinositol.

The present invention will hereinafter be described in more detail with reference to the following non-limitative working Examples.

EXAMPLE 1: PREPARATION OF COMPOUND II-1 (SCHEME 1)

1) Preparation of Intermediate 1

A natural diterpene, (7R,11R)-phytol (200 g) was dissolved in ethanol (1,000 ml), platinum oxide (1 g) was added to the solution and then the reaction mixture was stirred at room temperature for 6 hours in a hydrogen gas atmosphere. After completion of the reaction, insolubles were removed by filtration through Celite and the resulting filtrate was concentrated under reduced pressure to give 201 g of an intermediate 1 ((3RS,7R,11R)-phytanol) as an oily substance.

IR, $\gamma_{max}$ (cm$^{-1}$) (film): 3340 (br s), 2960 (s), 2930 (s), 2870 (s), 1465 (s), 1380 (s), 1370 (m), 1060 (s), 735 (w)

2) Preparation of Intermediate 2

Intermediate 1 (40 g) was dissolved in a carbon tetrachloride/acetonitrile/water (2:2:3) mixed solvent (700 ml), ruthenium trichloride·n hydrate (500 mg) and sodium metaperiodate (70 g) were added to the resulting solution and then the reaction mixture was vigorously stirred at room temperature for 4 hours. After completion of the reaction, insolubles were removed by filtration through Celite, the filtrate was diluted with methylene chloride, the organic phase was separated and then the water phase was extracted with methylene chloride. The organic phases were combined, washed once with water and dried over anhydrous sodium sulfate. The sodium sulfate was removed by filtration and the filtrate was concentrated under reduced pressure to give 29 g of an intermediate 2 ((3RS,7R,11R)-phytanoic acid) as an oily substance.

IR, $\gamma_{max}$ (cm$^{-1}$) (film): 3600-2400 (br m), 2960 (s), 2930 (s), 2870 (s), 1715 (s), 1465 (m), 1380 (m), 1370 (w), 1300 (m), 940 (w).

3) Preparation of Intermediate 3

To a solution of Intermediate 2 (30 g) in toluene (150 ml), there was added thionyl chloride (18 g) and the reaction mixture was stirred for 40 hours. After completion of the gas generation and the reaction, the solvent and the excess thionyl chloride were distilled off at ordinary pressure. The resulting residue was dried under reduced pressure to give 32 g of the desired intermediate 3 ((3RS, 7R,11R)-phytanoyl chloride) as an oily substance.

IR, $\gamma_{max}$ (cm$^{-1}$) (film): 2960 (s), 2930 (s), 2870 (s), 1800 (s), 1465 (s), 1380 (s), 1370 (m), 990 (m), 825 (s).

4) Preparation of Intermediate 4

To a solution of 3-benzyl-sn-glycerol (5.4 g; prepared by the method disclosed in Synthesis, 1985, p. 503) and diisopropylethylamine (10 g) in methylene chloride (100 ml), there was added a solution of Intermediate 3 (22.1 g) in methylene chloride (50 ml) and the reaction mixture was stirred at room temperature for 20 hours in the presence of a catalytic amount of 4-N,N-dimethylaminopyridine. After washing the reaction mixture with water and then a saturated aqueous solution of sodium chloride, it was dried over anhydrous sodium sulfate. The sodium sulfate was removed by filtration and the filtrate was concentrated under reduced pressure. The residue was purified by silica gel column chromatography (eluent: hexane/ethyl acetate=20/1) to give 19 g of an intermediate 4 (1,2-O-di-(3RS,7R,11R,15-tetramethylhexadecanoyl)-sn-glycero-3-benzyl ether) as an oily substance.

IR, $\gamma_{max}$ (cm$^{-1}$) (film): 3030 (w), 2960 (s), 2930 (s), 2870 (s), 1745 (s), 1500 (w), 1460 (s), 1380 (s), 1370 (m), 1245 (m), 1165 (s), 1120 (s), 1110 (sh), 730 (m), 695 (s).

5) Preparation of Compound II-1

To a solution of Intermediate 4 (10 g) in ethyl acetate (200 ml), there was added 5% palladium-carbon (1 g) and the reaction mixture was stirred at room temperature for 6 hours in a hydrogen gas atmosphere. After completion of the reaction, insolubles were removed by filtration through Celite and the resulting filtrate was concentrated under reduced pressure to give 8.6 g of the intended compound II-1 as an oily substance.

IR, $\gamma_{max}$ (cm$^{-1}$) (film): 3460 (br m), 2950 (s), 2920 (s), 2870 (s), 1745 (s), 1465 (s), 1380 (s), 1370 (sh), 1240 (m), 1165 (s), 1130 (m), 1100 (w), 1045 (m).

TLC (using Merck Art 5715 Plate; developer: hexane/ethyl acetate=3/1): Rf=0.51.

Elemental Analysis (for $C_{43}H_{84}O_5$): Calculated: C, 75.88; H, 12.35%; Found: C, 75.82; H, 12.30%.

EXAMPLE 2: PREPARATION OF COMPOUND II-2

Using farnesol, i.e., a naturally occurring sesquiterpene as a starting material, hydrogenation, oxidation of an alcohol into a carboxylic acid, conversion into an acid chloride, esterification and removal of benzyl group through hydrogenolysis were performed in this order in the same manner used in Example 1 to give a compound II-2 as an oily substance.

IR, $\gamma_{max}$ (cm$^{-1}$) (film): 3450 (br m), 2960 (s), 2930 (s), 2870 (s), 1745 (s), 1465 (s), 1380 (s), 1370 (m), 1240 (m), 1165 (s), 1045 (m).

TLC (using Merck Art 5715 Plate; developer: hexane/ethyl acetate=3/1): Rf=0.45.

Elemental Analysis (for $C_{33}H_{64}O_5$): Calculated: C, 73.33; H, 11.85%;

Found: C, 73.06; H, 12.04%.

EXAMPLE 3: PREPARATION OF COMPOUND II-3

Using geraniol, i.e., a naturally occurring monoterpene as a starting material, hydrogenation, oxidation of an alcohol into a carboxylic acid, conversion into an acid chloride, esterification and removal of benzyl group through hydrogenolysis were performed in this order in the same manner used in Example 1 to give a compound II-3 as an oily substance.

IR, $\gamma_{max}$ (cm$^{-1}$) (film): 3450 (br s), 2960 (s), 2930 (s), 2870 (s), 1745 (s), 1460 (s), 1380 (m), 1370 (sh), 1240 (s), 1165 (s), 1045 (s).

TLC (using Merck Art 5715 Plate; developer: hexane/ethyl acetate=3/1): Rf=0.40.

Elemental Analysis (for $C_{23}H_{44}O_5$): Calculated: C, 69.00; H, 11.00%; Found: C, 68.69; H, 11.23%.

EXAMPLE 4: PREPARATION OF COMPOUND III-1 (SCHEME 2)

1) To a solution of Compound II-1 (5 g) prepared in Example 1 and diisopropylethylamine (1.15 g) in methylene chloride (50 ml), there was added diphenylphosphorochloridate (2.4 g) and the reaction mixture was stirred at room temperature for one hour. After completion of the reaction, the reaction mixture was diluted with methylene chloride, washed with water, a saturated aqueous solution of sodium bicarbonate and a saturated aqueous solution of sodium chloride and then dried over anhydrous sodium sulfate. The sodium sulfate was removed by filtration and the filtrate was concentrated under reduced pressure to give 5.2 g of a compound III-5 as an oily substance.

IR, $\gamma_{max}$ (cm$^{-1}$) (film): 3060 (w), 2950 (s), 2930 (s), 2860 (s), 1745 (s), 1595 (s), 1490 (s), 1460 (s), 1380 (m), 1370 (sh), 1290 (m), 1190 (s), 1160 (m), 1060 (m), 960 (s), 755 (s), 735 (m), 685 (m).

2) Preparation of Compound III-1

To a solution of Compound III-5 (5.2 g) in ethyl acetate (60 ml), there was added platinum oxide (100 mg) and the reaction mixture was stirred at room temperature for 8 hours in a hydrogen gas atmosphere. After completion of the reaction, insolubles were removed by filtration through Celite and the filtrate was concentrated under reduced pressure to give 4.3 g of the intended compound III-1 (diphytanoyl phosphatidic acid) as an oily product.

IR, $\gamma_{max}$ (cm$^{-1}$) (film): 3600-2000 (br m), 2950 (s), 2920 (s), 2860 (s), 1745 (s), 1460 (s), 1380 (s), 1370 (sh), 1240 (s), 1165 (s), 1060 (s), 1020 (s).

Elemental Analysis (for $C_{43}H_{85}O_8P$): Calculated: C, 67.89; H, 11.18%; Found: C, 67.43; H, 11.33%.

An example of the preparation of Compound III-2 of the present invention will be given below as Example 5, but the synthetic method is not restricted to those given below. In other words, there may be used, for instance, a method comprising performing a reaction using phosphorodi(1,2,4-triazolide) as a phosphorylation agent and then hydrolyzing an active triester intermediate formed in the reaction system (C. B. Reese et al., Tetrahedron Lett., 1979, p. 5059); and a method comprising performing a reaction using benzylphosphorochloridate as a phosphorylation agent and then removing one of benzyl groups of the resulting phosphoric acid triester (A. E. Stepanov and V. I. Shvets, Chem. Phys. Lipids, 1980, 41, p. 21) and other various routes of synthesis.

EXAMPLE 5: PREPARATION OF COMPOUND III-2

To a solution of Compound II-1 (2 g) prepared in Example 1 and triethylamine (350 mg) in methylene chloride (10 ml), there was added phenylphosphorodichloridate (620 mg) and the reaction mixture was stirred at room temperature for 2 hour. After addition of water and stirring at room temperature for 30 minutes, the reaction mixture was diluted with methylene chloride, washed with water and a saturated aqueous solution of sodium chloride and then dried over anhydrous sodium sulfate. The sodium sulfate was removed by filtration and the filtrate was concentrated under reduced pressure. The resulting residue was purified by silica gel column chromatography (eluent: chloroform/methanol=9/1) to give 1.9 g of Compound III-2 as an oily substance.

IR, $\gamma_{max}$ (cm$^{-1}$) (film): 3600-2400 (br m), 3040 (w), 2950 (s), 2860 (s), 1745 (s), 1600 (w), 1460 (s), 1380 (s), 1370 (sh), 1240 (s), 1160 (s), 1030 (s), 740 (s), 695 (m).

Elemental Analysis (for $C_{49}H_{89}O_8P$): Calculated: C, 70.33; H, 10.61%; Found: C, 70.05; H, 10.75%.

EXAMPLE 6: PREPARATION OF COMPOUND III-3

Using farnesol, i.e., a naturally occurring sesquiterpene as a starting material, hydrogenation, oxidation of an alcohol into a carboxylic acid, conversion into an acid chloride, esterification, removal of benzyl group through hydrogenolysis, phosphorylation and removal of phenyl group through hydrogenolysis were performed in this order in the same manner used in Example 1 to give Compound III-3 as an oily substance.

IR, $\gamma_{max}$ (cm$^{-1}$) (film): 3600-2200 (br m), 2950 (s), 2920 (s), 2860 (s), 1745 (s), 1460 (s), 1380 (s), 1370 (sh), 1240 (s), 1165 (s), 1060 (s), 1020 (s).

Elemental Analysis (for $C_{33}H_{65}O_8P$): Calculated: C, 63.87; H, 10.48%; Found: C, 63.34; H, 10.32%.

EXAMPLE 7: PREPARATION OF COMPOUND III-4

Using geraniol, i.e., a naturally occurring monoterpene as a starting material, hydrogenation, oxidation of an alcohol into a carboxylic acid, conversion into an acid chloride, esterification, removal of benzyl group through hydrogenolysis, phosphorylation and removal of phenyl group through hydrogenolysis were performed in this order in the same manner used in Example 1 to give a compound III-4 as an oily substance.

IR, $\gamma_{max}$ (cm$^{-1}$) (film): 3550-2100 (br m), 2960 (s), 2930 (s), 2860 (s), 1745 (s), 1460 (s), 1380 (s), 1370 (m), 1240 (s), 1165 (s), 1060 (s), 1020 (s).

Elemental Analysis (for $C_{23}H_{45}O_8P$): Calculated: C, 57.50; H, 9.38%; Found: C, 57.01; H, 9.27%.

EXAMPLE 8: PREPARATION OF 1,2-O-DI-(3R,7R,11R,15-TETRAMETHYLHEXADECANOYL)-SN-GLYCERO-3-PHOSPHATIDYLCHOLINE (COMPOUND IV-1: IN FORMULA (IV), $R^4=R^5=R^6=CH_3$, N=3)

Intermediate 2 (3RS,7R,11R,15-tetramethylhexadecanoic acid; 936 mg) prepared in Example 1 was dissolved in 20 ml of chloroform, 618 mg of N,N-dicyclohexylcarbodiimide and 340 mg of N,N-dimethyl-4-aminopyridine were added to the solution and then the mixture was stirred for one hour. Subsequently, 638 mg of glycerophosphocholine-cadmium chloride complex was added to the reaction system and the resulting suspension was stirred for 4 days. The reaction solution was treated with an ion-exchange resin: Amberlite IR-120B and then purified on silica gel column chromatography. The fractions eluted with chloroform/methanol/water (60:35:5) were collected and concentrated under reduced pressure to give 270 mg of 1,2-O-di-(3RS,7R,11R,15-tetramethylhexadecanoyl)-sn-glycero-3-phosphatidylcholine (Compound IV-1) as a waxy substance.

Rf value (SiO$_2$ plate): 0.54 (CHCl$_3$:MeOH:-H$_2$O=60:35:5)

IR (KBr) (cm$^{-1}$): 2960 (s), 2930 (s), 2870 (s), 1740 (s), 1470 (s), 1380 (s), 1365 (sh), 1250 (s), 1165 (m), 1095 (s), 1065 (s), 970 (s), 820 (m).

$^1$H-NMR (CDCl$_3$—D$_2$O) δ(ppm): 0.75–0.95 (30H, complex d); 0.95–1.40 (40H, m); 1.9 (2H, br); 1.51 (2H, sep); 2.1 (2H, dd); 2.35 (2H, dd); 3.36 (9H, s); 3.84 (2H, br); 3.98 (2H, t); 4.15 (1H, br); 4.3–4.5 (4H, br+t).

FAB-MS (Pos.): 846 (M+H)$^+$.

EXAMPLE 9: PREPARATION OF 1,2-O-DI-(3,7,11-TRIMETHYLDODECANOYL)-SN-GLYCERO-3-PHOSPHATIDYLCHOLINE (COMPOUND IV-2: IN FORMULA (IV), $R^4=R^5=R^6=CH_3$, N=2)

The same procedures used in Example 1 were repeated except that 40 g of farnesol was used as a starting material to give 31 g of 3,7,11-trimethyldodecanoic acid.

There was dissolved, in 20 ml of chloroform, 726 mg of 3,7,11-trimethyldodecanoic acid, 618 mg of N,N-dicyclohexylcarbodii mide and 340 mg of N,N-dimethyl 4-aminopyridine were added to the solution and then the mixture was stirred for one hour. Subsequently, 638 mg of glycerophosphocholine-cadmium chloride complex was added to the reaction system and the resulting suspension was stirred for 5 days. The reaction solution was treated with an ion-exchange resin: Amberlite IR-120B and then purified on silica gel column chromatography. The fractions eluted with chloroform/methanol/water (60:35:5) were collected and concentrated under reduced pressure to give 220 mg of 1,2-O-di-(3,7,11-trimethyldodecanoyl)-sn-glycero-3-phosphatidylcholine (Compound IV-2) as a waxy substance.

IR (KBr) (cm$^{-1}$): 2960 (s), 2930 (s), 2870 (s), 1740 (s), 1470 (s), 1380 (s), 1365 (sh), 1250 (s), 1165 (m), 1095 (s), 1065 (s), 970 (s), 820 (m).

FAB-MS (Pos.): 706 (M+H)$^+$.

EXAMPLE 10: PREPARATION OF 1,2-O-DI-(3RS,7R,11R,15-TETRAMETHYLHEXADECANOYL)-SN-GLYCERO-2-DIMETHYLAMMONIOETHYL PHOSPHATE (COMPOUND IV-3: IN FORMULA (IV), $R^4=R^5=CH_3$, $R^6=H$, N=3)

There were dissolved, in 20 ml of chloroform, 3.4 g of Compound II-1 (1,2-O-di-(3RS,7R,11R,15-tetramethylhexadecanoyl)-sn-glycerol) prepared in Example 1, 1.2 g of 2-bromoethylphosphorodichloridate and 0.5 g of triethylamine and then the solution was stirred overnight. After distilling off the chloroform under reduced pressure, 20 ml of THF was added, then 0.5M sodium acetate solution was added to the solution and the solution was stirred for 4 hours. The THF was distilled off from the reaction solution, a dilute hydrochloric acid solution was added to acidify the solution followed by extraction with ether. The organic phase was washed with a saturated sodium chloride solution, dried over sodium sulfate and the ether was distilled off under reduced pressure. The resulting residue was dissolved by addition of 50 ml of chloroform, 50 ml of acetonitrile and 30 ml of dimethylamine and reaction was continued for one day under reflux condition. The reaction solution was distilled off under reduced pressure, 1.3 g of silver carbonate and 30 ml of methanol were added to the residue and the mixture was stirred for 3 hours. The reaction solution was filtered, the resulting filtrate was distilled off under reduced pressure and the residue was purified on silica gel column chromatography. The fractions eluted with chloroform/methanol/water (60:35:5) were collected and concentrated under reduced pressure to give 1.1 g of 1,2-O-di-(3RS,7R,11R,15-tetramethylhexadecanoyl)-sn-glycero-2-dimethylammonioethyl phosphate (Compound IV-3).

FAB-MS (Pos.): 832 (M+H)$^+$.

EXAMPLE 11: PREPARATION OF 1,2-O-DI-(3RS,7R,11R,15-TETRAMETHYLHEXADECANOYL)-SN-GLYCERO-2-TRIETHYLAMMONIOETHYL PHOSPHATE (COMPOUND IV-4: IN FORMULA (IV), $R^4=R^5=R^6=CH_2CH_3$, N=3)

To a solution of Compound II-1 (1,2-O-di-(3RS,7R,11R,15-tetramethylhexadecanoyl)-sn-glycerol) (3.4 g) and triethylamine (0.5 g) in chloroform, there was dropwise added 20 ml of a solution of 2-chloro-2-oxo-1,2,3-dioxaphosphorane (0.7 g) in chloroform at −20° C. After stirring overnight, the reaction solution was filtered and the filtrate was distilled off under reduced pressure. To the residue, there was added 2.1 g of triethylamine, the mixture was dissolved in 20 ml of dimethylformamide and the reaction was performed at 50° C. for 12 hours. The reaction solution was distilled under reduced pressure and then the resulting residue was purified on silica gel column chromatography. The fractions eluted with chloroform/methanol/water (60:35:5) were collected and concentrated under reduced pressure to give 0.51 g of 1,2-O-di-(3RS,7R,11R,15-tetramethylhexadecanoyl)-sn-glycero-2-triethylammonioethyl phosphate (Compound IV-4).

FAB-MS (Pos.): 930 (M+H)$^+$.

EXAMPLE 12: PREPARATION OF COMPOUND V-1 (SCHEME 1)

1) Preparation of Intermediate 5

To a solution of phenylphosphorodichloridate (1.37 g) in tetrahydrofuran (15 ml), there was added a solution of Compound II-1 prepared in Example 1 (4.0 g) and N-methylimidazole (530 mg) in tetrahydrofuran (20 ml) at room temperature and the reaction mixture was stirred for 30 minutes. Then a solution of N-t-butoxycarbonylethanolamine (1.0 g) and N-methylimidazole (530 mg) in tetrahydrofuran (20 ml) was added to the mixture and the reaction mixture was stirred for 2 hours. The reaction solution was poured in 100 ml of water and extracted with ethyl acetate. The organic phases obtained were combined, washed with water, a sodium bicarbonate aqueous solution and a saturated aqueous solution of sodium chloride and then dried over anhydrous sodium sulfate. The sodium sulfate was removed by filtration, the resulting filtrate was concentrated under reduced pressure to give a colorless oily substance. The product was purified on silica gel column chromatography (eluent: hexane/ethyl acetate=20/1 to 8/1) to give 2.89 g (yield 50.0%) of the intended intermediate 5 as colorless oily substance.

IR, $\gamma_{max}$ (cm$^{-1}$) (film): 3370 (m), 2950 (s), 2930 (s), 2860 (s), 1745 (s), 1720 (s), 1595 (m), 1380 (sh), 1370 (s), 1245 (s), 1165 (s), 1040 (s), 755 (s), 680 (w).

Elemental Analysis (for $C_{56}H_{102}NO_{10}P$): Calculated: C, 68.64; H, 10.42%; Found: C, 68.37; H, 10.78%.

2) Preparation of Compound V-1

Trifluoroacetic acid (15 ml) was added to a solution of Intermediate 5 (2.3 g) in methylene chloride (15 ml) and the reaction mixture was stirred at room temperature for 40 minutes. After confirming the completion of the reaction, the solvent was distilled off under reduced pressure to give a quantitative amount of Intermediate 5 from which t-Boc had been removed. The product was dissolved in ethyl acetate (30 ml), 50 mg of platinum oxide was added thereto and the reaction mixture was stirred for 20 hours in a hydrogen gas atmosphere. Insolubles were removed by filtration through Celite and the filtrate was concentrated under reduced pressure to give 1.9 g of the intended compound V-1 as viscous oily substance.

IR, $\gamma_{max}$ (cm$^{-1}$) (film): 3000-2200 (br m), 2960 (s), 2930 (s), 2860 (s), 1745 (s), 1620 (s), 1460 (s), 1380 (m), 1370 (sh), 1210 (s), 1155 (s).

FAB-MS: 826 (M+Na)$^+$.

EXAMPLE 13: PREPARATION OF COMPOUND V-1 (SCHEME 2)

1) Preparation of Intermediate 6

To a mixture of Compound III-1 (2 g) prepared in Example 4 and Z-serine benzyl ester (900 mg; prepared from Z-serine and benzylbromide in the usual manner), there was added dry pyridine and the mixture was dried by azeotropy. The dried product was dissolved in dry pyridine (10 ml), 2,4,6-trimethylbenzenesulfonyl chloride (900 mg) was added to the solution and the reaction mixture was stirred at room temperature for 15 hours. A proper amount of ice was added to the reaction mixture to stop the reaction followed by extraction with chloroform. After washing the organic phase with water, a saturated aqueous sodium bicarbonate solution and then a saturated aqueous solution of sodium chloride, the organic phase was dried over anhydrous sodium sulfate. The sodium sulfate was removed by filtration and the filtrate was concentrated under reduced pressure to give a crude product. The crude product was purified on silica gel column chromatography (eluent: methylene chloride/methanol=20/1) to give the intended intermediate 6 as oily substance.

IR, $\gamma_{max}$ (cm$^{-1}$) (film): 3600-2200 (br m), 2960 (s), 2930 (s), 2860 (s), 1745 (s), 1720 (s), 1600 (m), 1460 (s), 1380 (s), 1370 (sh), 1255 (s), 1160 (s), 1035 (s), 740 (m), 695 (m).

2) Preparation of Compound V-1

A catalyst (10% Pd-C; 100 mg) was added to a solution of Intermediate 6 (5.2 g) in ethyl acetate (60 ml) and the reaction mixture was stirred at room temperature for 8 hours in a hydrogen gas atmosphere. After completion of the reaction, insolubles were removed by filtration through Celite and the filtrate was concentrated under reduced pressure to give the title compound V-1 as viscous oily substance.

IR, $\gamma_{max}$ (cm$^{-1}$) (film): 3550-2000 (br m), 2960 (s), 2930 (s), 2860 (s), 1745 (s), 1720 (s), 1610 (s), 1460 (s), 1380 (s), 1370 (sh), 1220 (s), 1130 (s).

FAB-MS: 870 (M+Na)$^+$.

EXAMPLE 14: PREPARATION OF COMPOUND V-3

Compound II-1 and 1,2-O-isopropylideneglycerol as starting materials were subjected to phosphorylation and then deblocking in the same manner used in Example 13 to give 980 mg of the title compound V-3.

IR, $\gamma_{max}$ (cm$^{-1}$) (film): 3400-2150 (br m), 2960 (s), 2930 (s), 2860 (s), 1745 (s), 1460 (s), 1380 (s), 1370 (sh), 1250 (s), 1210 (s), 1150 (m), 1060 (s).

FAB-MS: 857 (M+Na)$^+$.

EXAMPLE 15: PREPARATION OF COMPOUND V-5

Compound II-1 and tetra-O-benzyl-myo-inositol as starting materials were subjected to phosphorylation and then deblocking in the method as disclosed in V. I. Shvets et al., Tetrahedron, 1973,29, p. 331 to give 280 mg of the title compound V-5 as colorless powder.

IR, $\gamma_{max}$ (cm$^{-1}$) (Nujol): 3350-2000 (br m), 2960 (s), 2940 (s), 2860 (s), 1745 (s), 1460 (s), 1380 (s), 1370 (sh), 1245 (s), 1220 (s), 1120 (s).

Elemental Analysis (for $C_{49}H_{95}O_{13}P \cdot H_2O$): Calculated: C, 62.55; H, 10.32%; Found: C, 62.03; H, 10.49%.

EXAMPLE 16: PREPARATION OF A LIPOSOME CONTAINING CARBOXY FLUORESCEINE AND LEAKAGE OF THE ENCAPSULATED COMPOUND

Compound II-2 (10 mg) and dipalmitoyl phosphatidylcholine (DPPC) (20 mg) was dissolved in chloroform (20 ml) and concentrated under reduced pressure to prepare a thin film. The film was fully dried under nitrogen atmosphere. A solution (3 ml) of carboxy fluoresceine in 3 ml of a buffer (200 mM/6 mM Tris-HCl, pH 7.4, containing 150 mM NaCl) was added and shaked with a vortex mixer for 15 minutes to prepare a coarse dispersion followed by sonication with a probe type ultrasonic generator for 10 minutes to prepare a liposome dispersion. The dispersion was subjected to gel permeation chromatography to remove non-encapsulated carboxy fluoresceine and to obtain the fraction of liposomes containing carboxy fluoresceine.

Particle size of the liposomes was measured. Those having average particle size of 200-300 nm were selected and diluted with 6 ml of a 6 mM Tris-HCl buffer containing 150 mM NaCl (pH 7.4 to adjust the lipid concentration to $2 \times 10^{-4}$M. Leakage of the encapsulated carboxy fluoresceine with time was monitored at various temperatures by fluorimetry. The results are shown in Table 1.

TABLE 1

| Time (min.) | Leaked carboxy fluoresceine (%) | | | | | |
|---|---|---|---|---|---|---|
| | 10 | 20 | 30 | 40 | 50 | 60 |
| Temp. | | | | | | |
| 37° C. | 1 | 1 | 1.5 | 2 | 2 | 2 |
| 45° C. | 2.5 | 3 | 3.5 | 3.5 | 4 | 4.5 |
| 75° C. | 8 | 12 | 16 | 20 | 25 | 28 |

COMPARATIVE EXAMPLE 1

The same procedures as in Example 16 were repeated except that dipalmitoyl phosphatidylcholine (DPPC) (30 mg) was substituted for Compound II-2 (20 mg) and DPPC (10 mg). The results are shown in Table 2.

TABLE 2

| Time (min.) | Leaked carboxy fluoresceine (%) | | | | | |
|---|---|---|---|---|---|---|
| | 10 | 20 | 30 | 40 | 50 | 60 |
| Temp. | | | | | | |
| 37° C. | 13 | 24 | 31 | 36 | 40 | 42 |
| 45° C. | 89 | 97 | 99 | 100 | 100 | — |

EXAMPLE 17

The compounds of the present invention were used in medicines, DDS and cosmetics and as a result, it was found that they were excellent in biological compatibility, dispersibility and chemical stability and that they could provide membranes having high flowability and high barrier properties as compared with conventional phospholipids.

The following drastic effects can be obtained by the use of the compounds of the present invention:

(1) The linkage between the glycerol and hydrocarbon chain moieties in the compounds of the invention is not an ether bond as observed in the biomembranes of archaebacteria, but an ester bond. Therefore, they can easily be synthesized and in particular mass-production thereof is very easy.

(2) The chain isoprenoid, whose structure and stereochemistry are known, as the starting material is easily available as compared with iso acid and anti-iso acid. This likewise makes the synthesis of the compounds easier.

(3) The compounds of the present invention have excellent properties such as good biological compatibility, dispersibility and chemical stability as well as ability of providing membranes having high flowability and high barrier properties. The combination of these properties cannot be achieved by the conventionally used phospholipids comprising only saturated fatty acids or those comprising unsaturated fatty acids.

(4) Moreover, the compounds of the present invention are amphipathic molecules which can serve as ingredients for lipid bilayers by themselves and which are capable of forming bilayers having phase transition temperatures of not more than room temperature. Therefore, the bilayers formed from the compounds of the invention have flowability quite similar to biomembranes and accordingly have various applications such as biomembrane models having specific characteristics in the field of biomembrane-mimetics studies and materials for liposomes as carrier for medicines.

We claim:

1. A glycerol derivative or the salt thereof represented by the following general formula (III):

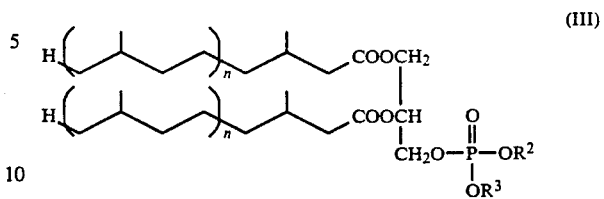

wherein n is 3, $R^2$ is a hydrogen atom and $R^3$ is a phenyl group, provided that the phosphoric acid residue may be in the form of a salt with a proper counter ion and, in respect of stereochemistry of asymmetric carbon atoms present in the molecule, the derivative may be either an optically active isomer or a acemic isomer.

2. A glycerol derivative or the salt thereof represented by the following general formula (III):

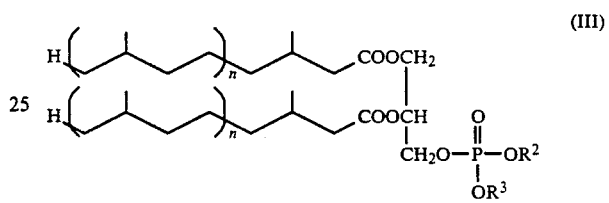

wherein n is 2, and $R^2$ and $R^3$ each represents a hydrogen atom, provided that the phosphoric acid residue may be in the form of a salt with a proper counter ion and, in respect of stereochemistry of asymmetric carbon atoms present in the molecule, the derivative may be either an optically active isomer or a racemic isomer.

3. A glycerol derivative or the salt thereof represented by the following general formula (III):

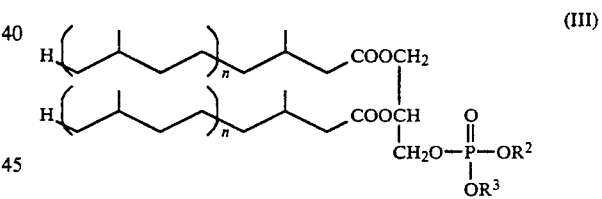

wherein n is 1, and $R^2$ and $R^3$ each represents a hydrogen atom, provided that the phosphoric acid residue may be in the form of a salt with a proper counter ion and, in respect of stereochemistry of asymmetric carbon atoms present in the molecule, the derivative may be either an optically active isomer or a racemic isomer.

4. A glycerol derivative or the salt thereof represented by the following general formula (IV):

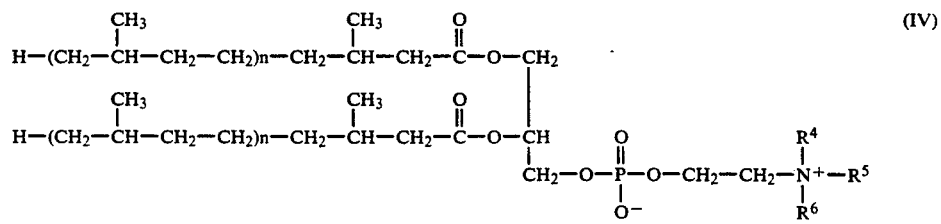

wherein n is 2 and $R^4$, $R^5$ and $R^6$ each represents a methyl group, provided that the phosphoric acid residue may be in the form of a salt with a proper counter ion and, in respect of stereochemistry of asymmetric carbon atoms present in the molecule, the derivative may be either an optically active isomer or a racemic isomer.

5. A glycerol derivative or the salt thereof represented by the following general formula (IV):

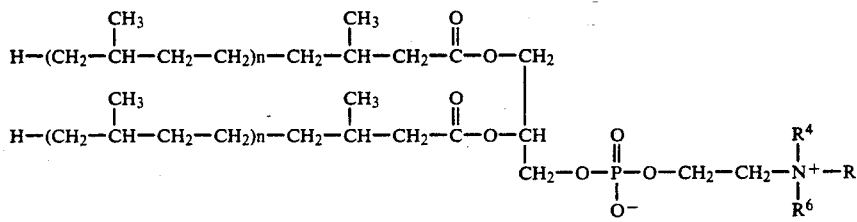

wherein n is 3, $R^4$ and $R^5$ each represents a methyl group, and $R^6$ represents a hydrogen atom, provided that the phosphoric acid residue may be in the form of a salt with a proper counter ion and, in respect of stereochemistry of asymmetric carbon atoms present in the molecule, the derivative may be either an optically active isomer or a racemic isomer.

6. A glycerol derivative or the salt thereof represented by the following general formula (IV):

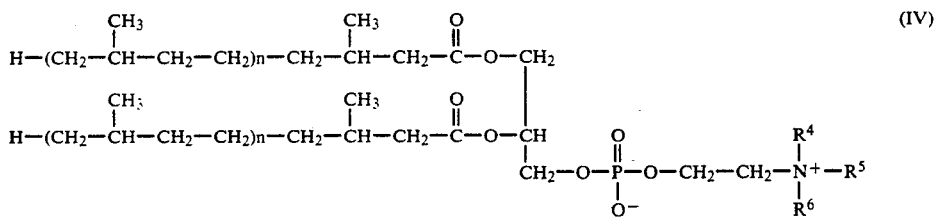

wherein n is 3, and $R^4$, $R^5$ and $R^6$ each represents an ethyl group, provided that the phosphoric acid residue may be in the form of a salt with a proper counter ion and, in respect of stereochemistry of asymmetric carbon atoms present in the molecule, the derivative may be either an optically active isomer or a racemic isomer.

7. A glycerol derivative represented by the following general formula (II):

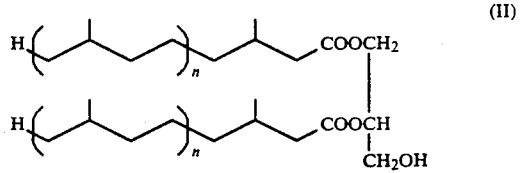

wherein n is 2, provided that, in respect of stereochemistry of asymmetric carbon atoms present in the molecule, the derivative may be either an optically active isomer or a racemic isomer.

8. A glycerol derivative represented by the following general formula (II):

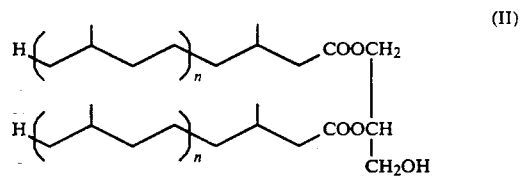

wherein n is 1, provided that, in respect of stereochemistry of asymmetric carbon atoms present in the molecule, the derivative may be either an optically active isomer or a racemic isomer.

* * * * *